United States Patent [19]

Bormann et al.

[11] Patent Number: 5,601,727

[45] Date of Patent: Feb. 11, 1997

[54] DEVICE AND METHOD FOR SEPARATING PLASMA FROM A BIOLOGICAL FLUID

[75] Inventors: Thomas J. Bormann, Melville; Vlado I. Matkovich; Thomas C. Gsell, both of Glen Cove; David B. Pall, Roslyn Estates, all of N.Y.

[73] Assignee: Pall Corporation, East Hills, N.Y.

[21] Appl. No.: 232,174

[22] PCT Filed: Nov. 3, 1992

[86] PCT No.: PCT/US92/09542

§ 371 Date: Aug. 2, 1994

§ 102(e) Date: Aug. 2, 1994

[87] PCT Pub. No.: WO93/08904

PCT Pub. Date: May 13, 1993

Related U.S. Application Data

[63] Continuation-in-part of Ser. No. 787,067, Nov. 4, 1991, abandoned.

[51] Int. Cl.⁶ .................. B01D 37/00; B01D 61/00
[52] U.S. Cl. .................. 210/767; 210/194; 210/433.1; 210/650; 210/651; 210/805
[58] Field of Search .................. 210/650, 651, 210/805, 767, 321.84, 321.75, 433.1, 194, 512.1; 422/101, 102; 604/6; 436/177, 178; 530/412, 414

[56] References Cited

U.S. PATENT DOCUMENTS

| | | | |
|---|---|---|---|
| 3,610,418 | 10/1971 | Calderwood | 210/336 |
| 3,623,610 | 11/1971 | Olsen et al. | 210/336 |
| 3,705,100 | 12/1972 | Blatt et al. | |
| 4,075,091 | 2/1978 | Bellhouse | |
| 4,178,248 | 12/1979 | Porter et al. | 210/409 |
| 4,212,742 | 7/1980 | Solomon et al. | 210/247 |
| 4,381,775 | 5/1983 | Nosé et al. | 604/6 |
| 4,604,208 | 8/1986 | Chu et al. | 210/636 |
| 4,619,639 | 10/1986 | Nosé et al. | 604/6 |
| 4,636,309 | 1/1987 | Bellhouse | 210/356 |
| 4,636,310 | 1/1987 | Bellhouse | 210/456 |
| 4,680,025 | 7/1987 | Kruger et al. | 604/6 |
| 4,746,436 | 5/1988 | Kopp et al. | 210/637 |
| 4,753,733 | 6/1988 | Ramstack | 210/636 |

(List continued on next page.)

FOREIGN PATENT DOCUMENTS

| | | |
|---|---|---|
| 1158988 | 12/1983 | Canada . |
| 1249110 | 1/1989 | Canada . |
| 0336483 | 10/1989 | European Pat. Off. . |
| 0399083 | 11/1990 | European Pat. Off. . |
| 0414006 | 2/1991 | European Pat. Off. . |
| 0464707 | 1/1992 | European Pat. Off. . |
| 0531540 | 3/1993 | European Pat. Off. . |
| 7901121 | 12/1979 | WIPO . |
| 8605410 | 9/1986 | WIPO . |
| 8904197 | 5/1989 | WIPO . |
| 9102555 | 3/1991 | WIPO . |
| 9104088 | 4/1991 | WIPO . |
| 9117809 | 11/1991 | WIPO . |
| 9207656 | 5/1992 | WIPO . |
| 9220383 | 11/1992 | WIPO . |
| 9308904 | 5/1993 | WIPO . |
| 9325295 | 12/1993 | WIPO . |

OTHER PUBLICATIONS

Transfusion, vol. 21, No. 5, 1981, Wiltbank, et al., "Filtration Plasmapheresis In Vivo", pp. 502–510.
Artificial Organs, vol. 13, (1):43–51, 1989, Beaudoin, et al., "Plasma Filtration in Couette Flow Membrane Devices".
Ann Clin Biochem, 28:55–59, 1991, van Oudheusden, et al., "A Multilayer Membrane . . . Primary Health Care".

*Primary Examiner*—John Kim
*Attorney, Agent, or Firm*—Leydig, Voit & Mayer

[57] ABSTRACT

A device and method for processing a biological fluid comprises directing the biological fluid tangentially or parallel to the face of a separation medium in at least one serpentine fluid flow channel such that a plasma-rich fluid passes through the separation medium and a plasma-depleted fluid passes tangentially to the surface of the separation medium.

14 Claims, 6 Drawing Sheets

U.S. PATENT DOCUMENTS

| | | | |
|---|---|---|---|
| 4,769,150 | 9/1988 | Ramstack | 210/636 |
| 4,800,022 | 1/1989 | Loenard | 210/636 |
| 4,806,247 | 2/1989 | Schoendorfer et al. | 210/416.1 |
| 4,845,132 | 7/1989 | Masuoka et al. | 210/490 |
| 4,880,548 | 11/1989 | Pall et al. | 210/767 |
| 4,888,115 | 12/1989 | Marinaccio et al. | 210/636 |
| 4,898,573 | 2/1990 | Takenaka et al. | 604/6 |
| 4,925,572 | 5/1990 | Pall | 210/767 |
| 4,933,092 | 6/1990 | Aunet et al. | 210/729 |
| 4,980,297 | 12/1990 | Haynes et al. | 436/178 |
| 4,995,967 | 2/1991 | Van Driessche | 210/94 |
| 5,008,012 | 4/1991 | Hagihara et al. | 210/321.8 |
| 5,013,437 | 5/1991 | Trimmer et al. | 210/321.78 |
| 5,049,268 | 9/1991 | Kopf | 210/321.75 |
| 5,069,789 | 12/1991 | Mohn et al. | 210/321.84 |
| 5,100,564 | 3/1992 | Pall et al. | 210/782 |
| 5,217,627 | 6/1993 | Pall et al. | 210/767 |
| 5,266,219 | 11/1993 | Pall et al. | 210/767 |

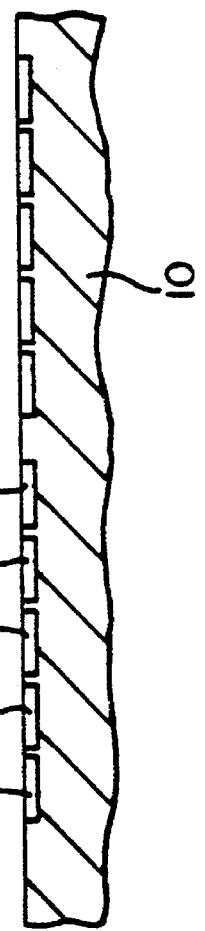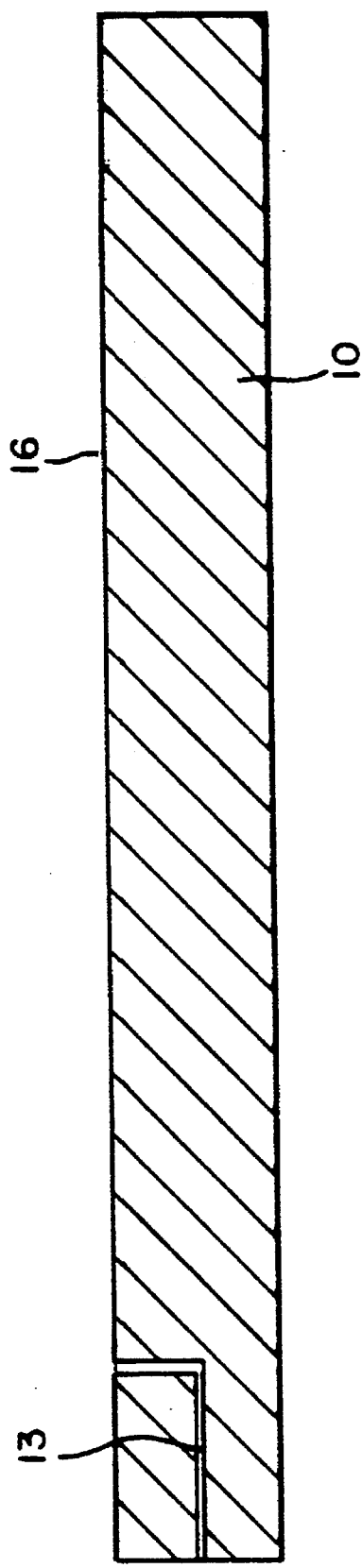

5,601,727

DEVICE AND METHOD FOR SEPARATING PLASMA FROM A BIOLOGICAL FLUID

CROSS-REFERENCE TO RELATED APPLICATIONS

This application is a U.S. national phase filing under 35 U.S.C. §371 of PCT/US92/09542, filed Nov. 3, 1992, and published as WO93/08904 May 13, 1993, which is a continuation-in-part of U.S. patent application Ser. No. 07/787,067, filed Nov. 4, 1991, now abandoned.

TECHNICAL FIELD

The present invention concerns a device and method for separating plasma from a biological fluid such as blood.

BACKGROUND OF THE INVENTION

An adult human contains about 5 liters of blood, of which red blood cells account for about 45% of the volume, white cells about 1%, and the balance being liquid blood plasma. Blood also contains large numbers of platelets. In view of the substantial therapeutic and monetary value of blood components such as red blood cells, platelets, and plasma, a variety of techniques have been developed to separate blood into its component fractions while ensuring maximum purity and recovery of each of the components.

Typically, donated blood is collected in a blood collection bag and separated by centrifugation into PRC and platelet-rich plasma (PRP) fractions, the latter of which is in current practice separated by a second centrifugation to provide plasma and PC. With respect to the second centrifugation step, the platelet concentrate is typically obtained from the PRP by "hard-spin" centrifugation (rotating at about 5000 G). This hard-spin compacts the platelets into a pellet or concentrate at the bottom of the test tube, flask, or bag. The plasma component is then removed or expressed to a separate bag or container, leaving the platelet component and some plasma behind. This platelet composition, which tends to form a dense aggregate, is subsequently dispersed to make PC. The dispersion step is usually carried out by gentle mixing, for example, by placing the bag on a moving table which rotates with a precessing tilted motion.

Platelet concentrate can also be prepared using apheresis of autologous blood. With this method, whole blood is removed from a single donor, and centrifuged into its component parts. The desired component is then harvested and the remainder of the blood is returned to the donor. This procedure allows collection of multiple units from one donor. Typically, a 2 to 3 hour apheresis procedure will produce a platelet product containing $3\times10^{11}$ platelets, equivalent to about six to ten units of random donor platelets, i.e., a typical transfusion unit. The common practice with respect to platelet concentrate is to transfuse a pool of six to ten units of platelets per administration, containing a total of about 300 to 700 ml of platelet concentrate.

Blood bank personnel have responded to the increased need for blood components by attempting to increase packed red cell (PRC) and platelet concentrate (PC) yields in a variety of ways. For example, in separating the PRP from PRC, blood bank personnel have attempted to ensure that the entire PRP fraction is recovered, but this may be counterproductive, since the PRP, and the PC subsequently extracted from it, are frequently contaminated by red cells, giving a pink or red color to the normally light yellow PC. The presence of red cells in PC is so highly undesirable that pink or red PC is frequently discarded, or subjected to recentrifugation, both of which increase operating costs and are labor intensive.

Additionally, freshly donated blood contains platelets varying in age from newly-formed to 9 days or more in age. Newly-formed platelets are larger, and are generally believed to be more active. Because the younger platelets are larger, they tend to sediment faster during the first centrifugation step, and consequently are present in larger numbers in the PRP nearest to the red cell interface. Thus, although it is desirable to reclaim a larger proportion of the younger, more active platelets, attempting to obtain a greater quantity poses a risk of contamination with red cells.

Typical techniques for processing platelets or platelet concentrate may reduce the yield and/or adversely affect the platelets. For example, as noted earlier, during the separation of PRP from PRC, it is difficult to efficiently obtain the maximum yield of platelets while preventing red cells from entering the plasma. Additionally, hard spin centrifugation and dispersion is labor intensive and it is believed that the forces applied during centrifugation may damage the platelets. For example, the hard-spin is potentially damaging to the platelets as it induces partial activation agglomeration of the platelets and may cause physiological damage. Such agglomeration requires several hours to resuspend the platelets in solution before they can be used for transfusion into a patient. Additionally, the several hour dispersion step is an undesirable delay, and is believed by many researchers to partially aggregate the platelet concentrate.

Furthermore, the hard-spin typically produces "distressed" platelets which partially disintegrate upon resuspension. Unfortunately, while mixing does prevent agglomeration, it encourages gas exchange by diffusion of oxygen through the walls of the bag (thereby controlling pH), and bathes the product in needed nutrients, this requires time, resulting in an increase in the number and size of microaggregates. Further, over time, gel-like bodies may be formed, which may comprise fibrinogen, degenerated protein, and degenerated nucleic acids, which may interfere with the separation of the platelets from the donated blood. Thus, some platelets are lost due to the process conditions.

Additionally, since platelets are notorious for being "sticky", an expression reflecting the tendency of platelets suspended in blood plasma to adhere to any non-physiological surface to which they are exposed, the recovery of platelets may be adversely affected during the preparation of platelet concentrate, regardless of the method of preparation. Furthermore, under many circumstances, platelets also adhere strongly to each other. Accordingly, in recovering platelets, it is desirable to restrict platelet loss to about 15% or less of the original platelet concentration.

Moreover, while leukocyte depletion of blood components for transfusion may decrease risk to the patient, when leukocytes are removed from, for example, platelet-rich plasma, which typically results in the production of a leukocyte-free platelet concentrate, the platelet component of the filtrate usually passes through a filter or separation device. In these systems, platelets may adhere to the surfaces of components of the separation device; such adhesion tends to cause substantial, and sometimes complete, removal of platelets from the filtrate. Furthermore, platelet concentrate present within the separation device at the completion of the separation process will be lost.

DISCLOSURE OF INVENTION

In describing the present invention, the following terms are used as defined below.

(A) Biological Fluid:

Biological fluids include any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, packed red cells (PRC), or buffy coat (BC); analogous blood products derived from blood or a blood component or derived from bone marrow; red cells separated from plasma and resuspended in physiological fluid; and platelets separated from plasma and resuspended in physiological fluid. The biological fluid may include leukocytes, or may be treated to remove leukocytes. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

B) Plasma-Depleted Fluid:

A plasma-depleted fluid refers to a biological fluid which has had some quantity of plasma-rich fluid (defined below) removed therefrom, e.g., the platelet-rich fluid or platelet component obtained when plasma is separated from PRP, or the fluid which remains after plasma is removed from whole blood. The separation of the plasma-rich fluid from the biological fluid produces a plasma-depleted fluid having an increased concentration of platelets and/or red cells on a volume basis. Typically, the plasma-depleted fluid is a platelet-containing fluid.

C) Plasma-Rich Fluid:

A plasma-rich fluid refers to the plasma portion or plasma component removed from a biological fluid, e.g., the plasma-rich fluid when plasma is separated from PRP, or the plasma which is removed from whole blood. The plasma-rich fluid separated from a biological fluid has an increased concentration of plasma on a volume basis. Typically, the plasma-rich fluid is the plasma-containing fluid that passes through a separation medium. Exemplary plasma-rich fluids include platelet-poor plasma or platelet-free plasma.

D) Separation medium:

A separation medium refers to a porous medium through which one or more biological fluids pass and which separates one component of the biological fluid from another. As noted in more detail below, the porous medium for use with a biological fluid may be formed from any natural or synthetic fiber or from a porous or permeable membrane (or from other materials of similar surface area and pore size) compatible with a biological fluid, typically a biological fluid containing platelets, e.g., whole blood or PRP. The surface of the fibers or membrane may be unmodified or may be modified to achieve a desired property.

Although the separation medium may remain untreated, the fibers or membrane are preferably treated to make them even more effective for separating one component of a biological fluid, e.g., plasma, from other components of a biological fluid, e.g., platelets or red cells. The separation medium is preferably treated in order to reduce or eliminate platelet adherence to the medium. Any treatment which reduces or eliminates platelet adhesion is included within the scope of the present invention. Furthermore, the medium may be surface modified in order to achieve a desired critical wetting surface tension (CWST), e.g., as disclosed in U.S. Pat. Nos. 4,880,548 and 5,100,564, and International Publication No. WO 92/07656 in order to increase the critical wetting surface tension (CWST) of the medium and to be less adherent of platelets. Defined in terms of CWST, a preferred range of CWST for a separation medium as provided by the present invention is above about 53 dynes/cm, typically above about 70 dynes/cm. The CWST of the separation medium may be dictated by its intended use. Further, the medium may be subjected to gas plasma treatment, an exemplary purpose for which is to reduce platelet adhesion.

The porous medium may be pre-formed, single or multi-layered, and/or may be treated to modify the surface of the medium. If a fibrous medium is used, the fibers may be treated either before or after forming the fibrous lay-up. It is preferred to modify the fiber surfaces before forming the fibrous lay-up because a more cohesive, stronger product is obtained after hot compression to form an integral element.

The separation medium may be configured in any suitable fashion, such as a flat sheet, a composite of two or more layers, a corrugated sheet, a web, hollow fibers, or a membrane.

F) Tangential flow filtration:

As used herein, tangential flow filtration refers to passing or circulating a biological fluid in a generally parallel or tangential manner to the surface of the separation medium.

The present invention provides a method for processing a biological fluid comprising: directing a biological fluid tangentially to the surface of a separation medium whereby plasma-rich fluid passes through the separation medium and plasma-depleted fluid passes tangentially across the separation medium.

The present invention provides a device for removing plasma from a biological fluid comprising: a housing having an inlet and first and second outlets and defining a first liquid flow path between the inlet and the first outlet and a second liquid flow path between the inlet and the second outlet; and a separation medium positioned inside the housing tangentially to the first flow path and across the second flow path, the separation medium being suitable for passing plasma therethrough.

The present invention provides a device for processing a biological fluid comprising: a housing having a first portion and a second portion; an inlet and a first outlet in the first portion and a first fluid flow path therebetween; a second outlet in the second portion and a second fluid flow path between the inlet and the second outlet; and a separation medium positioned inside the housing between the first portion and the second portion and tangentially to the first flow path and across the second flow path, the separation medium being suitable for passing plasma therethrough but not platelet-rich fluid.

The present invention provides a device for treating a biological fluid comprising: a separation medium having first and second external surfaces and being suitable for passing plasma therethrough; and a housing defining first and second flow paths, the separation medium being disposed within the housing wherein the first flow path extends tangentially to the first external surface of the separation medium and the second flow path extends from the first external surface through the separation medium to the second external surface.

The present invention provides for a system for processing a biological fluid comprising: a housing having an inlet and first and second outlets and defining a first liquid flow path between the inlet and the first outlet and a second liquid flow path between the inlet and the second outlet; a separation medium positioned inside the housing tangentially to the first flow path and across the second flow path, the separation medium being suitable for passing a plasma-rich fluid therethrough, and a container in fluid communication with the second outlet. The system may also include another container in fluid communication with the first outlet.

The invention involves the treatment of a biological fluid to non-centrifugally separate at least one component from the biological fluid, e.g., treating PRP to obtain plasma and PC, or separating plasma from whole blood. Processes and devices provided by the invention utilize a separation medium that allows the passage of plasma, but prevents passage of platelets and/or red cells, through the medium, thereby eliminating the need for "hard-spin" centrifugation or multiple centrifugations as processing steps. Tangential flow of a biological fluid parallel to the upstream surface of the separating medium permits the passage of plasma through the medium, while reducing the tendency for cellular components or platelets to adhere to the surface of the medium, thus assisting in the prevention of passage of platelets through the separation medium. The hydrodynamics of flow parallel to a surface are indeed believed to be such that during flow parallel to the surface, platelets develop a spin which causes them to be recovered from the surface.

The device and method of the present invention thus protect platelets and red blood cells from physiological damage, and directly and effectively minimize or eliminate loss or damage caused by the currently used centrifugal separation processes, by reducing or eliminating the exposure to harmful centrifugation. Furthermore, the platelets and/or red blood cells are not required to pass through yet another filtration device in order to be separated from PRP. A feature of the separation device of the invention, therefore, is the increased yield of clinically and therapeutically superior platelet concentrate and/or platelet-free (or platelet-poor) plasma.

Advantageous features of the devices and methods of the present invention include the separation of at least one component of a biological fluid from the rest of the fluid with minimal loss or activation of platelets. Platelet function is believed to be only minimally affected by the separation process, and platelet survival time within the patient is believed to be significantly longer. Further, because of the high cost and increased demand for both platelet preparations and for plasma, as well as the clinical need to deliver a maximum therapeutic dose, a device as provided by this invention can deliver a higher proportion of the platelets or plasma originally present in the sample. The present invention also provides for reclaiming a larger proportion of the younger, more active platelets in a sample.

This invention also provides for a device and method for separating platelet-poor plasma or platelet-free plasma from a biological fluid, such as PRP or from whole blood, without requiring rotation, spinning, or centrifugation to effect the separation. For example, the instant invention provides for the separation of plasma from whole blood without centrifugation. Additionally, the present invention provides for processing of PRP to form PC and plasma without hard-spin centrifugation.

The present invention further provides for maximum recovery of plasma from whole blood or from PRP.

Additionally, since some currently used procedures for processing biological fluid require several hours for completion, the present invention reduces processing time.

BRIEF DESCRIPTION OF DRAWINGS

FIG. 7 is a section of FIG. 6, along III—III.

FIG. 8 is a section of FIG. 6, along IV—IV.

MODES FOR CARRYING OUT THE INVENTION

The present invention involves the separation of one or more components from a biological fluid. As provided by the present invention, a biological fluid, particularly blood, is exposed to a separation medium suitable for passing plasma therethrough, but not platelets and/or red cells. Clogging of the separation medium by platelets and/or red cells is minimized or prevented.

The device of the present invention may be incorporated into a system which includes one or more containers in fluid communication with the inlet and/or outlets of the separation device.

Figure 1:
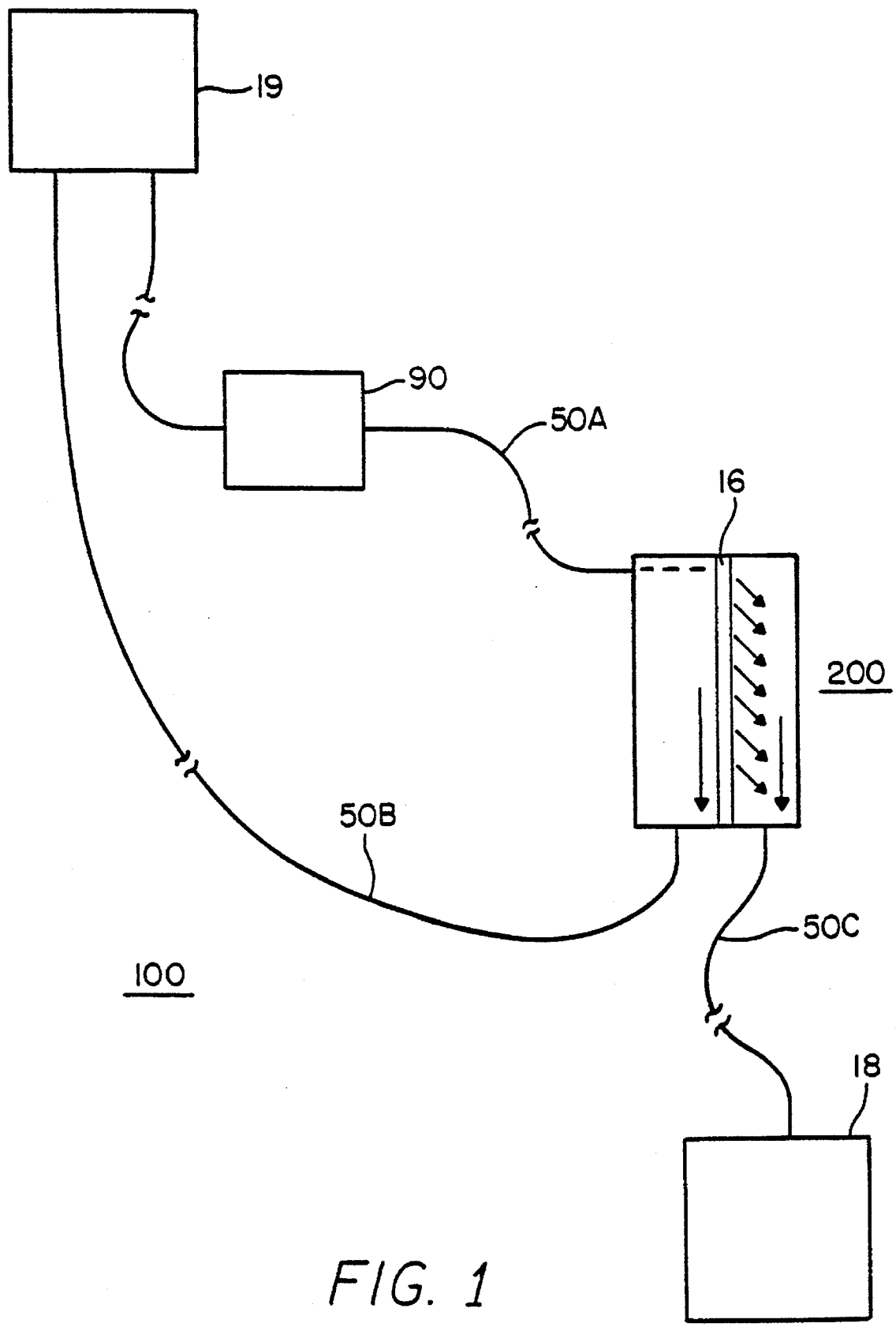
FIG. 1 is an elevation of an embodiment of the present invention.
Figure 2:
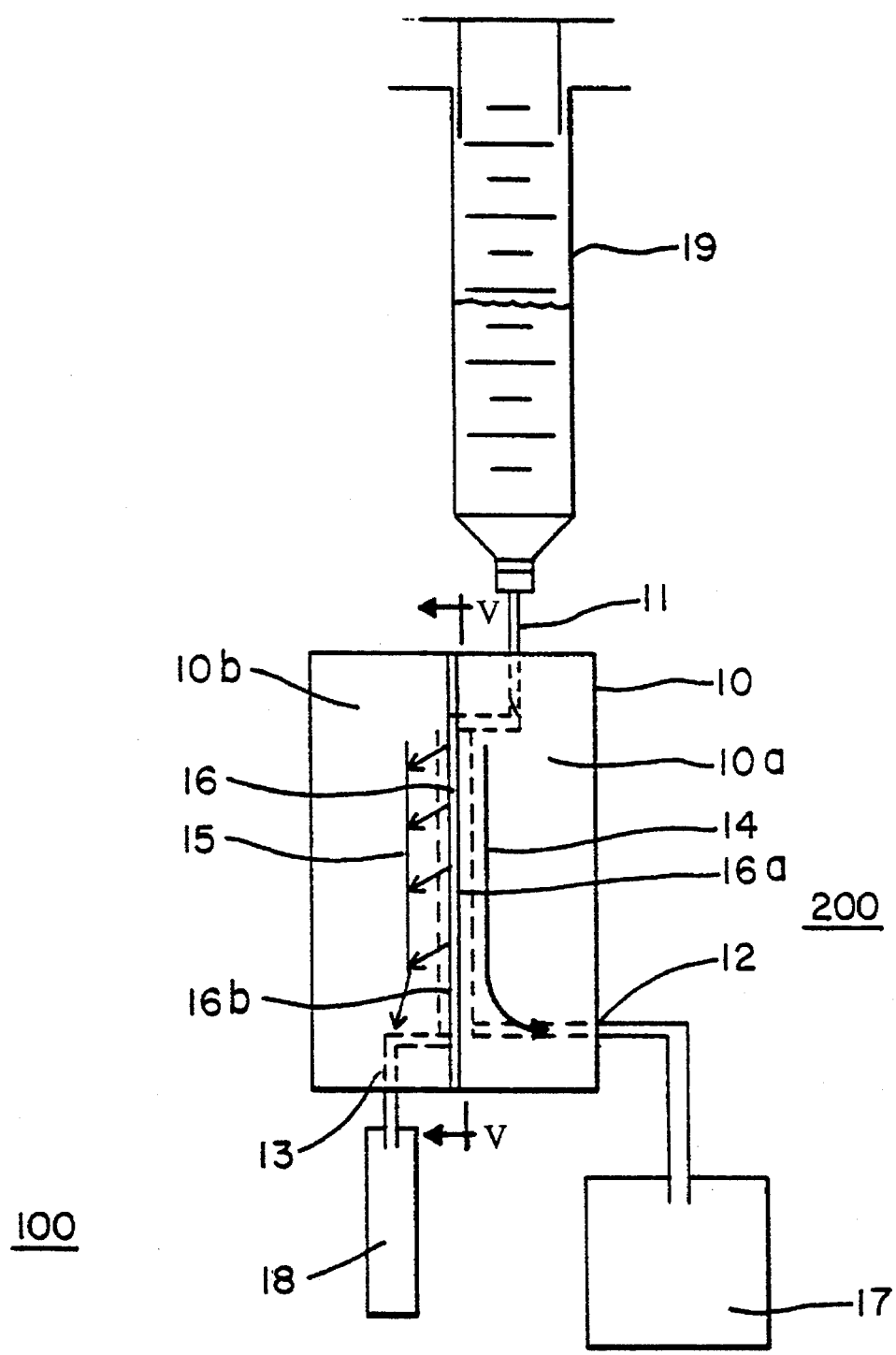
FIG. 2 is an elevation of another embodiment of the present invention.

Exemplary biological fluid processing systems, which may be closed and/or sterile systems, are shown in FIGS. 1 and 2. Biological fluid processing system 100 may include a first container such as a collection bag or syringe 19; a separation device 200 including a separation medium 16; a second container (first satellite bag) 18; a third container (second satellite bag) 17. The processing system 100 may also include at least one functional biomedical device, for example, a pump 90, and/or other functional biomedical devices, including filtration and/or separation devices (not shown).

The components of the biological fluid processing system may be in fluid communication through conduits. For example, as illustrated in FIG. 1, conduits 50A, 50B, and 50C may be used to provide fluid communication between the components of the system. The biological fluid processing system may also include a seal, valve, clamp, transfer leg closure, stopcock, or the like located within or on at least one of the conduits and/or the containers.

As illustrated in FIG. 2, a separation device as provided by the invention generally comprises a housing 10 which includes an inlet 11 and first and second outlets 12 and 13, respectively; a first fluid flow path 14 between the inlet 11 and the first outlet 12; and a second fluid flow path 15 between the inlet 11 and the second outlet 13. A separation medium 16 having first and second surfaces 16a, 16b is positioned inside the housing 10, the separation medium being positioned parallel to the first fluid flow path 14 and across the second fluid flow path 15.

As depicted in FIG. 2, in a separation device 200, the housing 10 includes first and second portions 10a and 10b, and the separation medium 16 is positioned inside the housing 10 between the first and second housing portions 10a, 10b. The first and second housing portions 10a, 10b may be joined in any convenient manner, for example, by ultrasonic or heat welding, an adhesive, a solvent, or one or more connectors.

Each of the components of the invention will now be described in more detail below.

Embodiments of the present invention may be configured in a variety of ways to ensure maximum contact of the biological fluid with the first surface 16a of separation medium 16 and to reduce or eliminate clogging on the first surface 16a of the separation medium. For example, the separation device includes one or more channels, grooves, conduits, passages, or the like which may be serpentine, parallel, curved, or a variety of other configurations facing the first surface 16a of the separation medium 16. Alternatively, the separation device may include a first shallow chamber facing the first surface 16a of the separation medium 16. The first chamber may include an arrangement of ribs which spread the flow of biological fluid over the entire first surface 16a of the separation medium 16.

The fluid flow channels may be of any suitable design and construction. For example, the channels may have a rectangular, triangular, or semi-circular cross section and a constant depth and width. Preferably, the channels have a rectangular cross section and vary in depth, for example, between inlet 11 and outlet 12.

Figure 3:
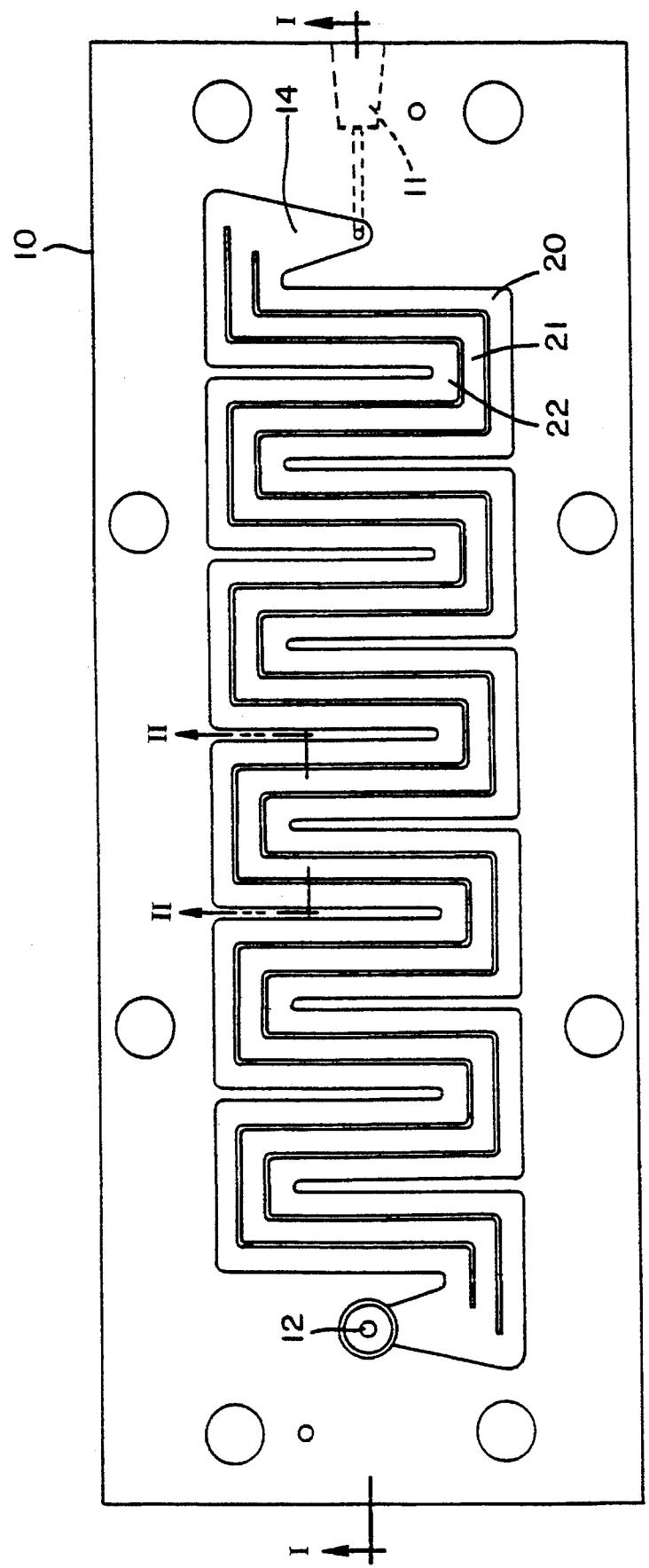
FIG. 3 is a cross-section of FIG. 2, along V—V, showing the first fluid flow path in a separation device as provided by the invention.
Figure 5:
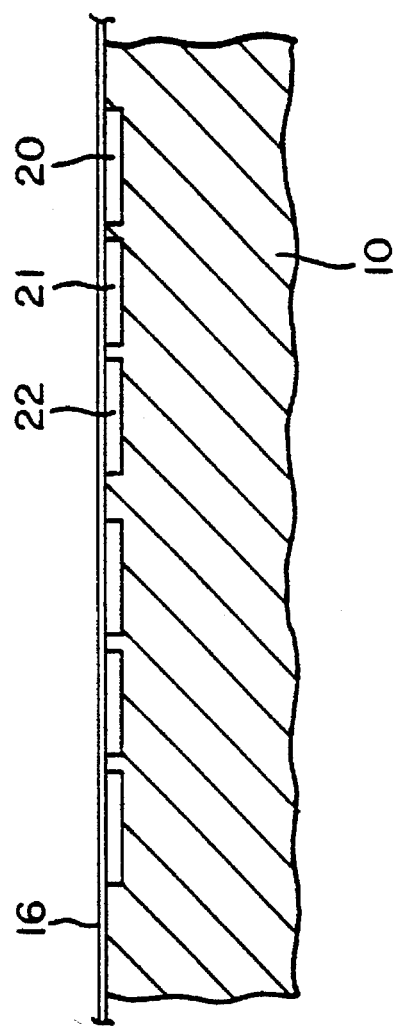
FIG. 5 is a section of FIG. 3, along II—II.
Figure 4:
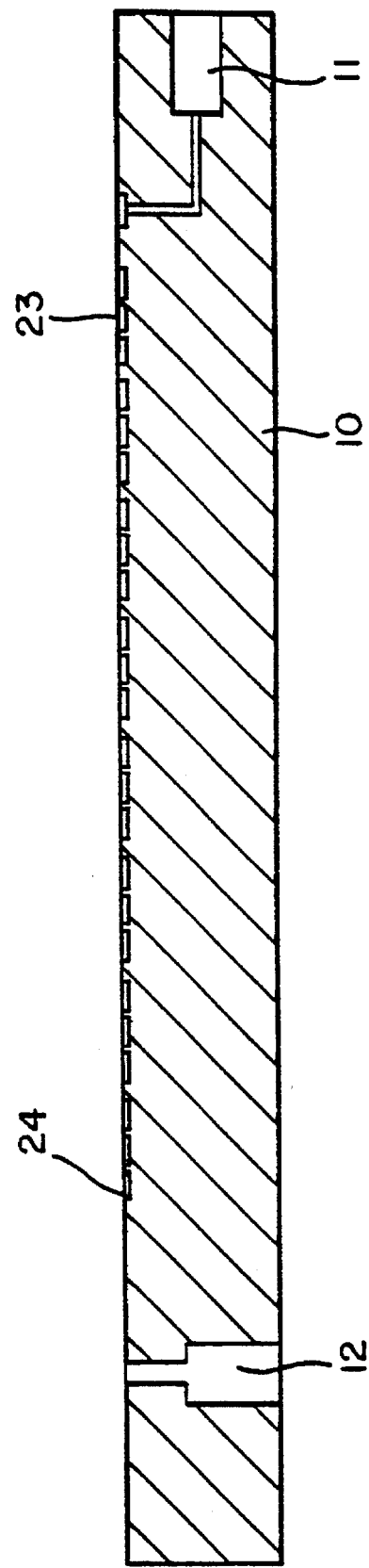
FIG. 4 is a section of FIG. 3, along I—I.

In the embodiment shown in FIGS. 3, 4, and 5, the inlet 11 of the housing 10 is connected to serpentine fluid flow channels 20, 21, and 22 which face the first surface 16a of the separation medium 16. These channels 20–22 separate the inlet flow of biological fluid into separate flow paths tangential to the first surface 16a of the separation medium 16. Extending along the first surface 16a, the serpentine fluid flow channels 20, 21, and 22 may be recombined at first outlet 12 of the housing 10.

Embodiments of the present invention may also be configured in a variety of ways to minimize back pressure across the separation medium 16 and to ensure a sufficiently high velocity of flow to the second outlet 12 to prevent fouling of surface 16a, while minimizing hold-up volume. The separation device may include an arrangement of ribs or may comprise one or more channels, grooves, conduits, passages, or the like which may be serpentine, parallel, curved, or have a variety of other configurations facing the second surface 16b of the separation medium. Alternatively, the separation device may include a second shallow chamber facing the second surface 16b of the separation medium 16.

Figure 6:
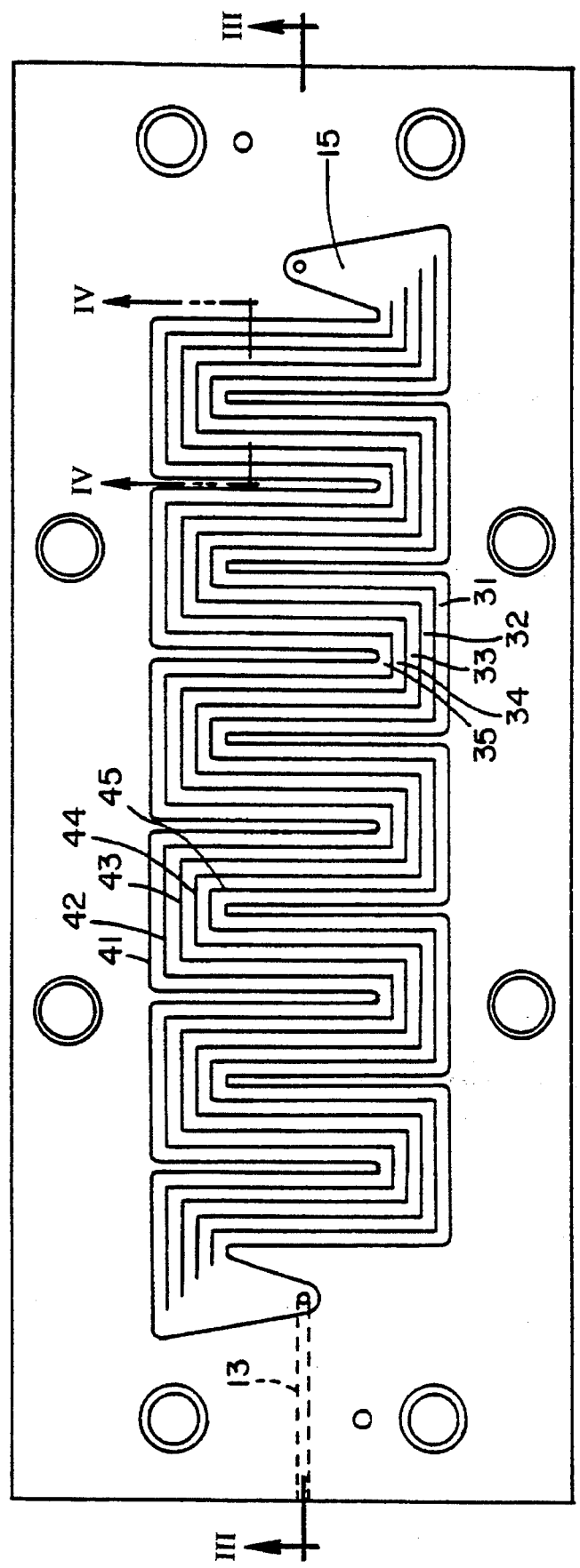
FIG. 6 is a cross-section of an embodiment of the invention showing the second fluid flow path in a separation device as provided by the invention.

The fluid flow channels may be of any suitable design and construction. For example, the channels may have a rectangular, semi-circular, or triangular cross section and a constant or variable depth and/or width. In the embodiment shown in FIGS. 6–8, several serpentine fluid flow channels 31, 32, 33, 34, and 35 face the second surface 16b of the separation medium 16. Extending along the second surface 16b, the serpentine fluid flow channels 31–35 may be recombined at the second outlet 13.

Ribs, walls, or projections 41, 42, 43, 44, and 45 may be used to define the channels 20–22, 31–35 of the first and second chambers and/or may support or position the separation medium 16 within the housing 10. In a preferred embodiment of the invention, there are more walls in the second chamber than in the first chamber to prevent deformation of the separation medium 16 caused by pressure differential through the separation medium.

An exemplary channel depth may be in the range from about 0.635 cm (about 0.250 inch) to about 0.0025 cm (about 0.001 inch). An exemplary channel width may be in the range from about 0.635 cm (about 0.250 in) to about 0.025 cm (about 0.010 inch).

The housing and the separation medium of the present inventive device may be of any suitable configuration and material. For example, the housing, including the channels, ribs, walls, and/or projections may be formed from a material that is substantially impermeable to the biological fluid and substantially unreactive with the biological fluid. In the illustrated embodiment, the channels are defined by three sides which are substantially impermeable to and substantially unreactive with the biological fluid, and one side, i.e., defined by the separation medium, that is permeable to the biological fluid. Alternatively, the channels may be defined by two substantially impermeable and substantially unreactive sides and two permeable sides. For example, in one configuration, the opposing sides of a channel may each face a separation medium, allowing plasma-rich fluid to flow through each separation medium, and plasma-depleted fluid to flow tangentially to each separation medium. In another variation, e.g., involving a half-round configuration, at least one side of the channel is substantially impermeable to and substantially unreactive with the biological fluid.

While the preferred device has one inlet and two outlets, other configurations can be employed without adversely affecting the proper functioning of the device. For example, multiple inlets for a biological fluid may be used so long as the biological fluid flows tangentially to the face of the separation medium. Alternatively, a single inlet and a single outlet may be used. For example, a separation device may be configured to provide for two liquid flow paths such that both liquid flow paths communicate with the inlet, but only one liquid flow path communicates with both the inlet and the outlet.

The separation medium may be arranged in the separation device in any suitable manner so long as the biological fluid flow tangential or parallel to the separation medium is maintained to a sufficient extent to avoid or minimize substantial platelet adhesion to the separation medium. One skilled in the art will recognize that platelet adhesion may be controlled or affected by manipulating any of a number of factors: velocity of the fluid flow, configuration of the channel, depth and/or width of the channel, varying the depth and/or varying the width of the channel, the surface characteristics of the separation medium, the smoothness of the medium's surface, and/or the angle at which the fluid flow crosses the face of the separation medium, among other factors. For example, the velocity of the first fluid flow is sufficient to remove platelets from the surface of the separation medium. Without intending to be limited thereby, a velocity in excess of about 30 cm/second has been shown to be adequate.

The velocity of the fluid flow may also be affected by the volume of the biological fluid, by varying the channel depth, and by varying the channel width. For example, as shown in FIG. 4, the channel depth may be varied from about 0.635 cm (about 0.250 in) in the region 23 near the inlet 11 to about 0.0025 cm (about 0.001 in) in the region 24 near the outlet 12. One skilled in the art will recognize that a desired velocity may be achieved by manipulating these and other elements. Also, platelets may not adhere as readily to a separation medium having a smooth surface as compared to a medium having a rougher surface.

A separation medium, as provided by the present invention, comprises a porous medium suitable for passing plasma-rich fluid therethrough. The separation medium, as used herein, may include but is not limited to polymeric fibers (including hollow fibers), polymeric fiber matrices, polymeric membranes, and solid porous media. Separation media in accordance with the invention separate plasma from a biological fluid containing platelets, typically whole blood or PRP, without allowing a substantial amount of platelets and/or red cells to pass therethrough.

A separation medium according to the invention preferably exhibits an average pore rating generally or intrinsically smaller than the average size of platelets. Preferably, platelets do not adhere to the surface of the separation medium, thus reducing pore blockage. The separation medium should also have a low affinity for proteinaceous components in the biological fluid such as PRP or whole blood. This enhances the likelihood that the plasma-rich fluid, e.g., platelet-free plasma, will exhibit a normal concentration of proteinaceous clotting factors, growth factors, and other needed components. The separation medium and device also enhances the likelihood that complement activation will be avoided.

In accordance with the invention, a separation medium formed of fibers may be continuous, staple, or melt-blown. The fibers may be made from any material compatible with a biological fluid containing platelets, e.g., whole blood or PRP, and may be treated in a variety of ways to make the medium more effective. Also, the fibers may be bonded, fused, or otherwise fixed to one another, or they may simply be mechanically entwined. A separation medium, as the term is used herein, may refer to one or more porous polymeric sheets, such as a woven or non-woven web of fibers, with or without a flexible porous substrate, or may refer to a membrane formed, for example, from a polymer solution in a solvent by precipitation of a polymer when the polymer solution is contacted by a solvent in which the polymer is not soluble. The porous, polymeric sheet will typically be microporous, e.g., having a substantially uniform, continuous matrix structure containing a myriad of small largely interconnected pores.

The separation medium of this invention may be formed, for example, from any synthetic polymer capable of forming fibers or a membrane. While not necessary to the apparatus or method of the invention, in one variation the polymer is capable of serving as a substrate for grafting with ethylenically unsaturated monomeric materials. In this variation, the polymer should be capable of reacting with at least one ethylenically unsaturated monomer under the influence of ionizing radiation or other activation means without the matrix being adversely affected. Suitable polymers for use as the substrate include, but are not limited to, polyolefins, polyesters, polyamides, polysulfones, polyarylene oxides and sulfides, and polymers and copolymers made from halogenated olefins and unsaturated nitriles. Preferred polymers are polyolefins, polyesters, and polyamides, e.g., polybutylene terephthalate (PBT) and nylon. In an embodiment, a polymeric membrane may be formed from a fluorinated polymer such as polyvinylidene difluoride (PVDF). The most preferred separation media are a microporous polyamide membrane or a polycarbonate membrane.

Exemplary separation media include but are not limited to those disclosed in International Publication No. WO 92/07656 and U.S. Pat. Nos. 4,886,836; 4,906,374; 4,964,989; 4,968,533; and 5,019,260, which may include separation media having a water permeability of up to about 0.023 L/min/Pa/m$^2$ (about 15.0 L/min/psid/ft$^2$).

Surface characteristics of a fiber or membrane can be modified by a number of methods, for example, by chemical reaction including wet or dry oxidation, by coating the surface through deposition of a polymer thereon, by grafting reactions which are activated by exposure to an energy source such as heat, a Van der Graff generator, ultraviolet light, or to various other forms of radiation, and by treatment of the fibers or membrane with a gas plasma. A typical method for treatment with a gas plasma utilizes radio frequency (RF) discharge, with or without one or more polymerizable species. A typical method for a grafting reaction uses gamma-radiation, for example, from a cobalt source.

Radiation grafting, when carried out under appropriate conditions, has the advantage of considerable flexibility in the choice of reactants, surfaces, and in the methods for activating the required reaction. Gamma-radiation grafting is particularly preferable because the products are very stable and have undetectably low aqueous extractable levels. Furthermore, the ability to prepare synthetic organic fibrous media having a CWST within a desired range is more readily accomplished using a gamma radiation grafting technique.

An exemplary radiation grafting technique employs at least one of a variety of monomers each comprising an ethylene or acrylic moiety and a second group, which can be selected from hydrophilic groups (e.g., —COOH, or —OH) or hydrophobic groups (e.g., a methyl group or saturated chains such as —CH$_2$CH$_2$CH$_3$). Grafting of the fiber or membrane surface may also be accomplished by compounds containing an ethylenically unsaturated group, such as an acrylic moiety, combined with a hydroxyl group, such as, hydroxyethyl methacrylate (HEMA). Use of HEMA as the monomer contributes to a very high CWST. Analogues with similar characteristics may also be used to modify the surface characteristics of fibers.

In a variation of the invention, the separation medium is surface modified by grafting thereon a hydroxyl-containing monomer to provide a separation medium having a low affinity for proteinaceous substances. For example, as described in U.S. Pat. No. 4,906,374, the separation medium, which is preferably a skinless membrane, may be surface modified using hydroxyl-containing unsaturated monomers, more typically monofunctional unsaturated monomers rich in pendant hydroxyl groups or groups capable of reacting to form hydroxyl groups, which are capable of undergoing polymerization and covalently bonding to the substrate under the influence of ionizing radiation. The most preferred hydroxyl-containing monomers are those in which the hydroxyl group is pendant, i.e., the group is not attached to a carbon atom which forms part of the polymer's backbone but is bound to a carbon atom that is separated from the backbone as, for example, a branching carbon atom. Suitable monomeric compounds should be substantially completely, if not totally, soluble in the solvents used. Solutions of the monomer compound may range in concentration of the monomer(s) from about 0.1 to about 5.0 percent, by weight, preferably about 0.2 to about 3.0 percent, by weight, based on the total weight of the solution.

In another variation of the invention, the separation medium is treated with a gas plasma, typically a low temperature gas plasma, with or without deposition of a polymeric substance formed by the plasma or introduced into the plasma. The term "plasma" or "gas plasma" is used generally to describe the state of an ionized gas. The use of the term "plasma" in this context should not be confused with "plasma" as it refers to a biological fluid. A gas plasma consists of high energy charged ions (positive or negative), electrons, and neutral species. As known in the art, a plasma may be generated by combustion, flames, physical shock, or, preferably, by electrical discharge, such as a corona or glow discharge.

In an exemplary gas plasma treatment technique, radio frequency (RF) discharge, a separation medium to be treated is placed in a vacuum chamber and the chamber is evacuated. Gas at low pressure is bled into the system through the gas inbleed until the desired gas pressure differential across the conduit is achieved. An electromagnetic field is generated by subjecting the gas to a capacitive or inductive RF electrical discharge. The gas absorbs energy from the electromagnetic field and ionizes, producing high energy particles. The gas plasma, as used in the context of the present invention, is exposed to the separation medium, thereby modifying the properties of the medium to provide it with characteristics not possessed by the untreated medium, e.g., improving its biocompatibility, and ability to reduce platelet adhesion.

The gas used to treat the surface of the medium may include inorganic and organic gases used alone or in combination according to need. In addition, the gas may be a vaporized organic material, such as an ethylenic monomer to be plasma polymerized or deposited on the surface of the fiber. One example of a suitable gas is oxygen.

Typical parameters for treatment with a gas plasma may include power levels from about 10 to about 3000 watts. The RF frequency may include about 1 kHz to about 100 MHz. Exposure times may include about 5 seconds to about 12 hours. The gas pressures may include about 0.001 to 100 torr; and a gas flow rate of about 1–2000 standard cc/min.

In accordance with the invention, the separation medium may be surface modified, typically by radiation grafting or gas plasma treatment, in order to achieve the desired performance characteristics, whereby platelets are concentrated with a minimum of medium blocking. It may also be desirable to surface modify the separation medium such that the resulting plasma solution contains essentially all of its native proteinaceous constituents. Exemplary membranes having a low affinity for proteinaceous substances are disclosed in U.S. Pat. Nos. 4,886,836; 4,906,374; 4,964,989; 4,968,533; and 5,019,260.

Suitable membranes in accordance with an embodiment of the invention may be skinless microporous membranes and may be produced by, for example, a solution casting method.

For the separation of about one unit of whole blood, a typical separation device as provided by the invention includes an effective pore size smaller than platelets on the average, typically less than about 4 micrometers, preferably less than about 2 micrometers.

A typical separation device as provided by the invention includes a separation medium having an effective surface area in the range of about 1.94 cm$^2$ to about 194 cm$^2$ (about 0.3 in$^2$ to about 30 in$^2$). As used herein, the term effective surface area refers to the surface area contacted by the biological fluid.

A preferable ratio of the wetted surface area of the fluid flow channel to the volume of the channel (A/V) is in the range of about 6.3 cm$^{-1}$ to about 866 cm$^{-1}$ (about 16 in$^{-1}$ to about 2,200 in$^{-1}$).

The permeability of the separation medium is sufficient to allow the passage of a desirable amount of a fluid therethrough at a reasonable pressure in a reasonable amount of time. With respect to biological fluid, a preferred permeability is in the range of from about 0.00078 L/min/Pa/m$^2$ to about 0.023 L/min/Pa/m$^2$ (about 0.5 to about 15.0 L/min/psid/ft$^2$). With respect to plasma, a preferred permeability is in the range of from about 0.00078 L/min/Pa/m$^2$ to about 0.0078 L/min/Pa/m$^2$ (about 0.5 to about 5.0 L/min/psid/ft$^2$), more preferably in the range of about 0.0011 L/min/Pa/m$^2$ to about 0.0047 L/min/Pa/m$^2$ (about 0.7 to about 3.0 L/min/psid/ft$^2$).

The permeability and size of a typical separation device as provided by the present invention is preferably sufficient to produce about 160 cc to about 240 cc of plasma at reasonable pressures (e.g., less than about 6.9×10$^5$ Pa (100 psi), more preferably, less than about 1.38×10$^5$ (20 psi) in a reasonable amount of time (e.g., less than about one hour).

As provided by the present invention, all of these typical parameters may be varied to achieve a desired result, e.g., varied preferably to minimize platelet loss, to maximize plasma-rich fluid production, and/or to establish a certain flow rate.

The separation device may be positioned in the system of the instant invention in a variety of locations. For example, as illustrated in FIG. 2, it may be located downstream of first container 19 and upstream of second container 18 and third container 17 respectively. Alternatively, as illustrated in FIG. 1, it may be interposed between first container 19 and second container 18.

A system as provided by the present invention may be used in conjunction with other functional biomedical devices, including filtration and/or separation devices, e.g., a device for removing leukocytes from a platelet-containing fluid or platelet concentrate. Exemplary functional biomedical devices are disclosed in U.S. Pat. Nos. 4,880,548, 4,925,572, and 5,100,564; and International Publication Nos. WO 92/07656 and WO 91/17809. A functional biomedical device, as used herein, refers to any of a number of devices, assemblies, or systems used in the collection and/or processing of biological fluids, such as whole blood or a blood component. Exemplary functional biomedical devices include biological fluid containers, such as collection, transfer, and storage bags; conduits and connectors interposed between the containers; clamps, closures, and the like; air or gas inlet or outlet devices; a debubbler; a pump; and a red cell barrier device or assembly. The functional biomedical device may also include a device for destroying biological contaminants, such as a high intensity light wave chamber, or a device for sampling a biological fluid.

The present inventive device may similarly be part of an apheresis system. The biological fluid to be processed, the platelet-rich solution, and/or the platelet-poor solution may be handled in either a batch or continuous manner. The sizes, nature, and configuration of the present inventive device can be adjusted to vary the capacity of the device to suit its intended environment.

The processing of biological fluid in the context of the present invention may take place at any suitable time, which may be soon after donation. For example, when the biological fluid is donated whole blood, it is typically processed as soon as practicable in order to maximize the number of components derived and to maximize blood component viability and physiological activity. Early processing may more effectively reduce or eliminate contaminating factors, including, but not limited to, leukocytes and microaggregates.

A method as provided by the invention may be described in more detail with reference to FIGS. 1 and 2. Typically, a unit of a biological fluid, (e.g., donor's whole blood, or PRP) may be received into a first container 19 such as a collection bag or syringe for processing.

Movement of the biological fluid through the device and/or through the system may be effected by maintaining a pressure differential between a container such as a collection bag or a syringe containing the biological fluid, and the destination of the biological fluid (e.g., a container such as a satellite bag), to cause the fluid to flow in a desired direction. Exemplary means for creating this pressure differential may be by gravity head, applying pressure to the container (e.g., by hand or with a pressure cuff), by placing the satellite bag in a chamber which establishes a pressure differential between the satellite bag and the collection bag, e.g., a vacuum chamber or by a pump. It is intended that the present invention is not to be limited by the means of creating the pressure differential.

With reference to FIGS. 1 and 2, the biological fluid is processed by directing it from the container 19 to separation medium 16 so that the biological fluid flows tangentially to the surface of the separation medium. Directing the biological fluid to the separation medium may include channelling the biological fluid tangentially to the surface of the separation medium such that a plasma-rich fluid passes tangentially across the separation medium and a plasma-rich fluid passes through the separation medium.

As noted above, establishing a tangential flow of the biological fluid being processed parallel with or tangential to the face of the separation medium minimizes platelet collection within or passage through the separation medium. As provided by the invention, the tangential flow can be induced by any mechanical configuration of the flow path which induces a high local fluid velocity at the immediate membrane surface. The tangential flow of the biological fluid may be directed tangential or parallel to the face of the separation medium in any suitable manner, preferably utilizing a substantial portion of the separation medium surface while maintaining a sufficient flow to ensure that the platelets do not clog or block the pores of the separation medium.

The flow of the biological fluid is preferably directed tangentially or parallel to the face of the separation medium through the use of at least one fluid flow channel which is designed to maximize utilization of the separation medium, ensure a sufficiently total area contact between the biological fluid and the separation medium, and maintain a sufficient flow of biological fluid to minimize or prevent platelet adhesion to the separation medium. Most preferably, several (e.g., three or more) uniform, serpentine, fluid flow channels are utilized so as to induce a high local fluid velocity along the entire immediate membrane surface and to fix the separation medium in place and to prevent sagging of the membrane due to the applied pressure. In the embodiments illustrated in FIGS. 3 and 6, three fluid flow channels are utilized in the first flow path, and five fluid flow channels are utilized in the second fluid flow path.

The fluid flow channels may be of any suitable design and construction and preferably are variable with respect to depth to maintain Optimal pressure and fluid flow across the face of the separation medium. By providing fluid flow channels, e.g., serpentine fluid flow channels, the biological fluid flows through each channel at a velocity high enough to sweep clean the surface of the separation medium and prevent platelets, red cells, or other material from fouling the medium. By providing several channels, the velocity of the fluid is uniformly high across the entire surface of the separation medium. Consequently, no eddys or stagnant areas of the biological fluid develop where platelets, red cells, or other material may settle upon, stick to, and foul the separation medium. Fluid flow channels may also be utilized on the side of the separation medium opposite the biological fluid tangential flow to control the flow rate and pressure drop of a platelet-poor fluid, such as plasma.

In an exemplary method, the biological fluid enters inlet 11 of housing 10 as shown in FIG. 2. From the inlet 11, the fluid enters the channels 20–22 of the first chamber and passes tangentially or parallel to the first surface 16a of the separation medium 16 on the way to the first outlet 12 via the first fluid flow path 14. Plasma-rich fluid passes through the separation medium 16, and enters the channels 31–35 of the second chamber, and is directed toward the second outlet 13 via the second fluid flow path 15.

As the biological fluid continues along the first flow path 14 tangentially or parallel to the first surface 16a of the separation medium 16, more and more plasma-rich fluid crosses the separation medium 16. A plasma-depleted fluid, e.g., a platelet-containing fluid, then exits the housing 10 at the first outlet 12 while plasma-rich fluid exits the housing 10 at the second outlet 13. Typically, the plasma-rich fluid may be stored in a region separated from the separation medium in order to avoid possible reverse flow of the plasma-rich fluid back across the separation medium to the plasma-depleted fluid.

The plasma-rich fluid exiting at the second outlet 13, and/or the plasma-depleted fluid exiting at the first outlet 12, may be further processed. For example, as shown in FIG. 2, additional processing may include collecting the fluids in separate containers, such as first satellite bag 18 and second satellite bag 17. As shown in FIG. 1, additional processing may include re-directing the plasma-depleted fluid to the separation medium to deplete additional amounts of plasma. The plasma-depleted fluid may be repeatedly recirculated through the separation device, e.g., until the plasma-depleted fluid contains a pre-determined amount or concentration of platelets.

The biological fluid may be supplied in any suitable quantity consistent with the capacity of the overall device and by any suitable means, e.g., in a batch operation by, for example, a blood bag connected to an expressor or a syringe, or in a continuous operation as part of, for example, an apheresis system.

In order that the invention herein described may be more fully understood, the following examples are set out regarding use of the present invention. These examples are for illustrative purposes only and are not to be construed as limiting the present invention in any manner.

EXAMPLE 1

Whole blood was collected into an Adsol™ donor set and was processed under standard conditions to yield a unit of PRP. The PRP was then filtered to remove leukocytes using a filter device described in U.S. Pat. No. 4,880,548. The removal efficiency was <99.9%.

The filtered PRP unit was then placed in a pressure cuff to which a pressure of 300 mm Hg was applied. The tubing exiting the bag (clamped closed at this point) was connected to the inlet port of a separation device as shown in FIGS. 3–6. A microporous polyamide membrane having a pore rating of 0.65 microns was used as the separation medium in the device. The area of the membrane was about 17.4 square centimeters. The depth of the first fluid flow path channels decreased from about 0.03 cm near the inlet to about 0.01 cm near the outlet. The depth of the second fluid flow path channels was about 0.025 cm. The width of the channels was 0.084 cm. The outlet ports of the device were connected to tubing which allowed the volume of fluid exiting the device to be measured and saved for analysis.

The test of the present invention was started by opening the clamp and allowing PRP to enter the device. Clear fluid (plasma) was observed to exit one port, and turbid fluid (platelet concentrate) exited the other port. The duration of the test was 42 minutes, during which 154 ml of plasma and 32 ml of platelet concentrate was collected. The concentration of platelets in the plasma was found to be $1.2\times10^4/\mu l$, while the concentration of platelets in the platelet concentration was found to be $1.4333\ 10^6/\mu l$.

The above results indicate that PRP can be concentrated to a useful level, and platelet-poor plasma recovered, in a reasonable time by a device provided by the invention.

EXAMPLE 2

A sample of 450 ml of whole blood was collected under standard conditions from a human donor and placed in a typical flexible plastic blood bag. An analysis of the whole blood sample indicates that it contained about 203 ml plasma. A 2 cc whole blood sample was withdrawn from the bag in a 5 cc syringe and attached to the inlet port of a device as provided by the invention as shown in FIG. 2.

The present inventive device included a serpentine fluid flow path with a channel length of 32.5 cm, a constant width of 0.081 cm, and a constant depth of 0.013 cm. The fluid flow path was of a "C" cross-section and, on its open side, contacted a microporous polycarbonate membrane having a pore rating of 0.4 microns which served as the separation medium. About 26.4 cm$^2$ of the microporous membrane were thereby part of the fluid flow path and were capable of being contacted by the whole blood sample or processed fluid as it passed through the device in the fluid flow path. Fluid flowed through the separation medium at a rate of 0.2 ml/min. The entire whole blood sample was processed in about 2 minutes. Air in the syringe was used to drive any hold-up through the device.

At the conclusion of the processing, a total of about 1.6 cc of turbid fluid (red cell containing fraction) and 0.4 cc of clear fluid was collected from the processing of the whole blood sample. An analysis of the clear fluid indicated that it was plasma.

The above results indicate that plasma can be removed from whole blood in a reasonable time through the use of the present invention.

EXAMPLE 3

A sample of 450 ml of whole blood is collected under standard conditions from a human donor and placed in a typical flexible plastic blood bag. An analysis of the whole blood sample indicates that the hematocrit is 37%, indicating that the sample includes about 283.5 cc plasma and 166.5 cc red cells. A 2 cc whole blood sample is withdrawn from the bag in a 5 cc syringe and attached to the inlet port of a device comprising a serpentine fluid flow path similar to that described in Example 2.

At the conclusion of the processing a total of about 0.75 cc of turbid fluid (red cell containing fraction) and 1.25 cc of clear fluid is collected from the processing of the whole blood sample. An analysis of the clear fluid indicates that it is plasma.

The above results indicate that plasma can be efficiently removed from whole blood in a reasonable time through the use of the present invention.

EXAMPLE 4

A source bag and a satellite bag were connected to a separation device and a peristaltic pump in a configuration similar to that of FIG. 1. The source bag contained a unit of leukocyte depleted PRP (approximately 200 ml). Tubing connected the source bag to the inlet port of the separation device, and, to provide for recirculation, tubing connected the first outlet port of the separation device to the source bag. Additionally, tubing connected the second outlet port of the separation device to the satellite bag.

A peristaltic pump was associated with the tubing between the source bag and the inlet port of the separation device to provide for fluid flow.

The satellite bag was placed on a scale so that the amount of plasma entering the bag could be monitored. The peristaltic pump was activated at a flow rate of 25 cc/min and PRP was drawn from the source bag into the device. Clear fluid (plasma) exited the second port and entered the satellite bag. Turbid fluid (containing platelets) exited the first port and was recirculated into the source bag. The source bag was periodically squeezed to increase the mixing of the platelets in the fluid.

After approximately 35 minutes, about 150 ml of plasma was collected in the satellite bag and about 50 ml of platelet concentrate was collected in the source bag.

The above results indicate that platelet concentrate and platelet-poor plasma can be recovered in a reasonable time, using recirculation of fluid by a device provided by the invention.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for processing a biological fluid comprising:
    directing a biological fluid tangentially to the surface of a separation medium in at least one serpentine fluid flow channel whereby plasma-rich fluid passes through the separation medium and plasma-depleted fluid passes tangentially across the separation medium.

2. The method of claim 1 further comprising recirculating plasma-depleted fluid to the separation medium.

3. The method of claim 1 further comprising passing the plasma-rich fluid through at least one flow channel.

4. The method of claim 1 comprising passing the biological fluid through two or more serpentine fluid flow channels.

5. A device for removing plasma from a biological fluid comprising:
    a housing having an inlet and first and second outlets and defining a first fluid flow path comprising at least one serpentine fluid flow channel between the inlet and the first outlet and a second fluid flow path between the inlet and the second outlet; and
    a separation medium positioned inside the housing tangentially to the first fluid flow path and across the second fluid flow path, the separation medium being suitable for passing plasma therethrough.

6. The device of claim 5 wherein said first fluid flow path comprises two or more serpentine fluid flow channels.

7. The device of claim 5 wherein said second fluid flow path comprises at least one fluid flow channel.

8. The device of claim 5 wherein said at least one serpentine fluid flow channel is deeper near the inlet than near the first outlet.

9. The device of claim 5 wherein said at least one serpentine fluid flow channel decreases in depth over the length of the channel in the fluid flow direction.

10. The device of claim 7 wherein said fluid flow channel is a serpentine fluid flow channel.

11. The device of claim 10 wherein said second fluid flow path comprises two or more serpentine fluid flow channels.

12. A method for decreasing the plasma content of a biological fluid comprising:

directing a biological fluid through the device of claim 8 tangentially to the surface of the separation medium whereby a platelet-poor fluid passes through the separation medium and a platelet-rich fluid is recovered.

13. The method of claim 12 further comprising directing the biological fluid tangentially to the surface of the separation medium at substantially constant velocity.

14. The method of claim 12 further comprising recirculating platelet-rich fluid through the device.

\* \* \* \* \*